United States Patent [19]

Rose et al.

[11] 4,270,004
[45] May 26, 1981

[54] CHEMICAL PROCESS FOR THE PREPARATION OF 4-(6¹-METHOXY-2¹-NAPHTHYL)BUTAN-2-ONE

[75] Inventors: Carl J. Rose, London; David Miller, Herts, both of England

[73] Assignee: Beecham Group Limited, England

[21] Appl. No.: 83,837

[22] Filed: Oct. 11, 1979

Related U.S. Application Data

[62] Division of Ser. No. 973,748, Dec. 26, 1978, Pat. No. 4,247,709.

[30] Foreign Application Priority Data

Jan. 7, 1978 [GB] United Kingdom .................. 602/78

[51] Int. Cl.³ ..................... C07C 45/65; C07C 67/313
[52] U.S. Cl. ........................................ 568/314; 560/53
[58] Field of Search ...................... 260/590 R, 590 E; 560/51, 53; 568/314

[56] References Cited

U.S. PATENT DOCUMENTS 3,917,718  11/1975  Collins ............................. 260/590 R
4,029,713   6/1977  Parker ............................. 260/590 R

FOREIGN PATENT DOCUMENTS 1474377 of 0000 United Kingdom ................ 260/590 R

OTHER PUBLICATIONS

Bowman, J. Chem. Soc., 1950, pp. 323–329.

Jones, Organic Reactions, vol. 15, pp. 249–253, (1967).

Primary Examiner—Natalie Trousof
Assistant Examiner—James H. Reamer
Attorney, Agent, or Firm—Jacobs & Jacobs

[57] ABSTRACT

The present invention relates to a process for the preparation of 4-(6¹-methoxy-2¹-naphthyl)butan-2-one and to certain compounds for use in that process.

British patent specification No. 1,474,377 discloses inter alia that 4-(6¹-methoxy-2¹-naphthyl)butan-2-one possesses useful anti-inflammatory activity. A particularly favored process has now been discovered that can be used to produce 4-(6¹-methoxy-2¹-naphthyl)butan-2-one in particularly good yield.

The present invention provides a process for the preparation of 4-(6¹-methoxy-2¹-naphthyl)butan-2-one which process comprises the hydrogenation of a compound of the formula (I):

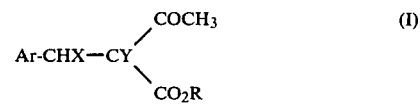

wherein Ar is a 6-methoxy-2-naphthyl group; X and Y are each hydrogen atoms or together represent a second bond between the carbon atoms to which they are attached; and R is a group such that —CO₂R represents an ester group convertible by hydrogenation to a CO₂H group.

9 Claims, No Drawings

CHEMICAL PROCESS FOR THE PREPARATION OF 4-(6¹-METHOXY-2¹-NAPHTHYL)BUTAN-2-ONE

REFERENCE TO RELATED APPLICATIONS

This application is a divisional of Ser. No. 973,748 filed Dec. 26, 1978; now U.S. Pat. No. 4,247,709.

The present invention relates to a process for the preparation of 4-(6¹-methoxy-2¹-naphthyl)butan-2-one and to certain compounds for use in that process.

British patent specification No. 1,474,377 discloses inter alia that 4-(6¹-methoxy-2¹-naphthyl)butan-2-one possesses useful anti-inflammatory activity. A particularly favoured process has now been discovered that can be used to produce 4-(6¹-methoxy-2¹-naphthyl)butan-2-one in particularly good yield.

The present invention provides a process for the preparation of 4-(6¹-methoxy-2¹-naphthyl)butan-2-one which process comprises the hydrogenation of a compound of the formula (I):

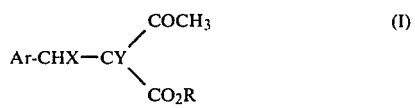

wherein Ar is a 6-methoxy-2-naphthyl group; X and Y are each hydrogen atoms or together represent a second bond between the carbon atoms to which they are attached; and R is a group such that —CO$_2$R represents an ester group convertible by hydrogenation to a CO$_2$H group.

Suitable groups R include benzyl and substituted benzyl groups such as those of the sub-formula (a), benzyhydryl groups (b) and trityl groups (c).

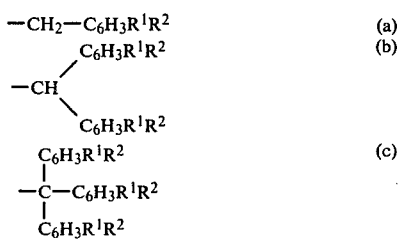

wherein R$^1$ and R$^2$ are independently hydrogen or halogen atoms or C$_{1-3}$ alkyl, C$_{1-3}$ alkoxyl, nitro or the like group.

Any substituent R$^1$ or R$^2$ present on a phenyl ring is most suitably para- or meta-. Halogen atoms are more suitably bromine or chlorine atoms. In general not more than one substituent R$^1$ or R$^2$ is present on the phenyl group.

Particularly suitable groups R include benzyl, p-methoxybenzyl, p-bromobenzyl, p-methylbenzyl, p-chlorobenzyl and the like.

A preferred group R is the benzyl group.

The hydrogenation of the compound of the formula (I) may be carried out employing a low, medium or high pressure of hydrogen, for example from about 0.5 to 4 atmospheres of hydrogen but in general in order to prevent over reduction it is preferred to use a pressure of about 0.9 to 1.5 atmospheres of hydrogen, for example 1 atmosphere pressure.

The hydrogenation will be carried out in the presence of a catalyst, for example a noble metal catalyst such as palladium which is preferred. Suitable forms of palladium catalysts include palladium on charcoal, palladium on barium sulphate, palladium on calcium carbonate or the like. Other noble metal catalysts which may be used include rhodium, for example as rhodium on alumina. Platinum is not normally preferred.

Suitable solvents for the reaction include lower alcohols, esters, halohydrocarbons and the like and ketonic solvents such as methylisobutylketone or acetone. Particularly suitable solvents include esters such as methyl acetate and ethyl acetate of which ethyl acetate is preferred.

The reaction may be performed at a depressed, ambient or elevated temperature, for example about 0° to 35° C. and most conveniently at ambient temperature.

Once the reaction is over (for example as judged by tlc or cessation of hydrogen uptake) the desired compound may be obtained by filtering off the catalyst and removal of the solvent, for example by evaporation under reduced pressure.

If desired the compound thus obtained may be further purified by recrystallisation, for example from aqueous ethanol.

It will be realised by the skilled worker that the foregoing reaction may proceed via a corresponding compound of the formula (II):

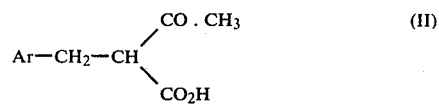

wherein Ar is as defined in relation to formula (I).

The compound of the formula (II) decarboxylates spontaneously under the above described conditions.

The hydrogenation of the compound of the formula (I) is preferably carried out on a compound wherein X and Y represent a second bond joining the carbon atoms to which they are attached in view of the convenient preparation of such compounds by reaction of 6-methoxy-2-naphthaldehyde with a compound of the formula (III):

wherein R is as defined in relation to formula (I).

Thus from an alternative aspect this invention provides a process for the preparation of 4-(6¹-methoxy-2¹-naphthyl) butan-2-one which comprises (a) the reaction of 6¹-methoxy-2-naphthaldehyde with a compound of the formula (III) as hereinbefore defined to yield a compound of the formula (I) as hereinbefore defined wherein X and Y represent a second bond joining the carbon atoms to which they are attached; and thereafter hydrogenating the thus produced compound of the formula (I).

The reaction of the aldehyde and ester will be carried out in an inert medium such as a halohydrocarbon, hydrocarbon or ether solvent or the like. Suitable solvents for this condensation include benzene and cyclohexane, a particularly preferred solvent being cyclohexane.

The reaction may be carried out at any convenient non-extreme depressed, ambient or elevated temperature, for example 0° to 100° C. but in general slightly elevated temperatures such as 35°–80° C. are preferred.

It is also convenient to remove the water formed during the reaction, for example by the inclusion of a dehydrating agent or the use of a Dean-Stark apparatus or the like.

A small quantity of a catalyst such as an amine salt, for example piperidinium acetate or the like, may be employed.

The desired intermediate may be obtained by evaporation of the solvent. Alternatively the addition of diethyl ether may be used to precipitate the intermediate.

The thus formed enone ester may be used with or, more conveniently, without further purification.

In a further aspect this invention provides the compounds of the formula (IV):

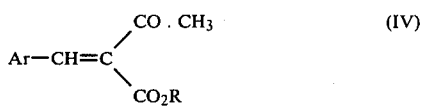

wherein Ar and R are as defined in relation to formula (I).

A particularly favoured compound of the formula (IV) is 3-benzyloxycarbonyl-4-(6¹-methoxy-2¹-naphthyl)but-3-en-2-one.

The advantages of the synthesis of this invention over the process which employs non-hydrogenolysable esters include (a) higher overall yields; (b) one reaction stage less thereby involving less handling of compounds and apparatus and less opportunity for impurity formation; (c) efficient scale up and (d) the production of a solid intermediate of type (IV) which may be purified and/or more conveniently stored if desired.

The following Examples illustrate the invention; the Description is included for comparison purposes:

Description 1 Preparation of 4-(6'-Methoxy-2'-naphthyl)butan-2-one using Ethyl Acetoacetate

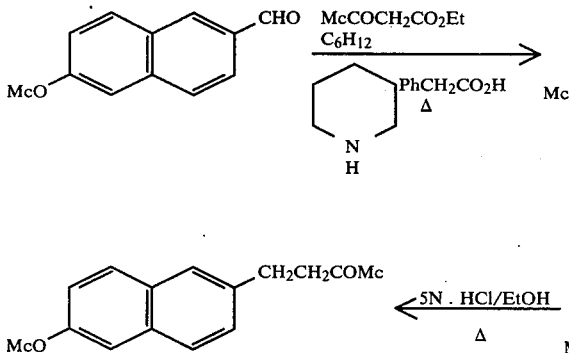

6-Methoxy-2-naphthaldehyde (93.0 g., 0.5 mole), ethyl acetoacetate (71.5 g., 0.55 mole), cyclohexane (1.0 litre), piperidine (5.0 ml) and phenylacetic acid (1.5 g.) were heated under reflux for 22 hours, water being removed using a Dean-Stark apparatus. Solvent was removed under reduced pressure to give crude 3-ethoxycarbonyl-4-(6¹-methoxy-2¹-naphthyl) but-3-en-2-one (164.8 g.) as a viscous oil which was used directly for the next stage.

The viscous oil (162.9 g.) in ethanol (1050 ml) was hydrogenated at room temperature and atmospheric pressure in the presence of 10% palladium on charcoal (15.9 g.). After 5½ hours, uptake of hydrogen was complete and the catalyst was filtered off, washed with ethanol (100 ml), and the ethanol filtrates containing 3-ethoxycarbonyl-4-(6¹-methoxy-2¹-naphthyl)butan-2-one used in the next stage.

90% of the above filtrate (i.e. containing 0.45 moles of product assuming 100% reaction) (1200 ml) and 5N.HCl (470 ml) were refluxed for 7 hours. Removal of ethanol under reduced pressure gave a buff coloured solid which was dissolved in ethyl acetate (1.0 litre) and the aqueous layer separated and washed with more ethyl acetate (100 ml). The combined organic solutions were washed with sodium bicarbonate solution to pH 8 (800 ml), water, and dried (Na₂SO₄).

Removal of solvent under reduced pressure gave a buff coloured greasy solid (103.6g.) which was crystallised from 80% ethanol/water (588 ml) and then ethanol (275 ml) to give 4-(6¹-methoxy-2¹-naphthyl) butan-2-one (55.9g., 54.5%) m.p. 80.5°–81°.

Larger scale reactions (one 27 moles of 6-methoxy-2-naphthaldehyde) have resulted in much reduced overall yields (37-41%) of final product.

Example 1 Preparation of 4-(6'-Methoxy-2'-naphthyl)butan-2-one using Benzyl Acetoacetate

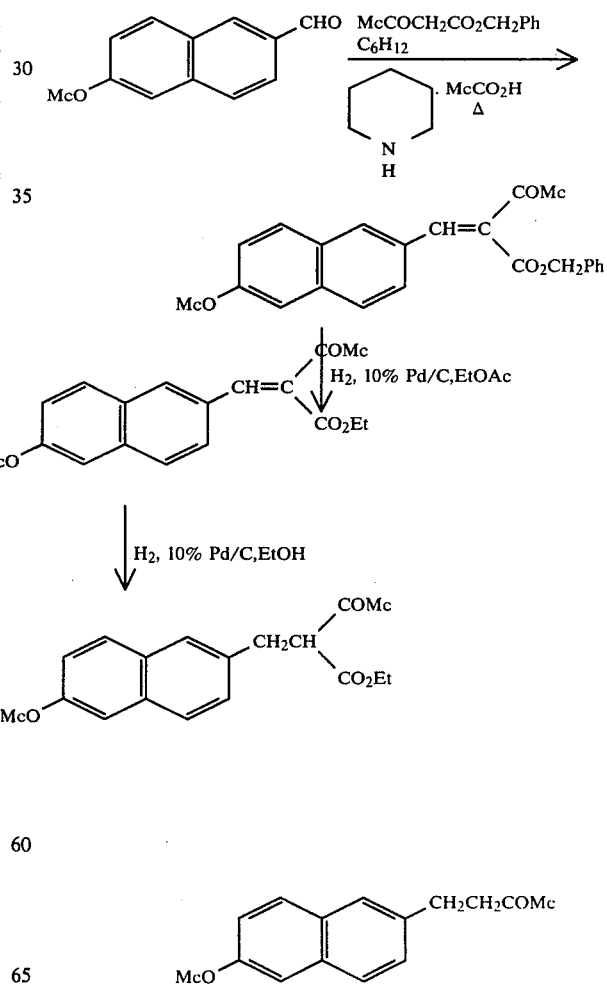

6-Methoxy-2-naphthaldehyde (37.2 g., 0.2 mole), benzyl acetoacetate (40.0 g., 0.21 mole), cyclohexane (500 ml) and piperidinium acetate (2.0 g.) were refluxed for 4 hours, water being removed using a Dean-Stark apparatus. Ether (250 ml) was added and the mixture cooled to 5° for 16 hours giving 3-benzyloxycarbonyl-4-(6$^1$-methoxy-2$^1$-naphthyl)but-3-en-2-one (58.0 g., 80.6%) m.p. 88°–90° as a yellow solid. This was not purified further but was used directly in the next stage.

The solid (58.0 g.) was shaken with 10% palladised charcoal (4.0 g.) in ethyl acetate (500 ml) under hydrogen until the reaction was complete. Removal of catalyst by filtration followed by evaporation of the filtrate gave a white solid (36.0 g.) which was recrystallised from 80% ethanol/water (200 ml) to give 4-(6$^1$-methoxy-2$^1$-naphthyl)butan-2-one [30.6 g., 83.3% (overall yield from aldehyde 67.1%]m.p. 81°.

Larger scale reactions (on 20 moles of 6-methoxy-2-naphthaldehyde) maintained the overall yield of 67% final product.

EXAMPLE 2

Preparation of 4-(6$^1$-methoxy-2$^1$-naphthyl)butan-2-one

The hydrogenation described in Example 1 was repeated using the alternative solvents methyl acetate, acetone and methyl isobutyl ketone (MIBK). Hydrogenation was carried out until uptake was complete. The results were as follows:

| Solvent | Methyl acetate | Acetone | MIBK |
| --- | --- | --- | --- |
| Reaction time | 2 hours | 3 hours | 4.5 hours |
| Yield | 79% | 68.5% | 63% |

EXAMPLE 3

Preparation of 4-(6$^1$-methoxy-2$^1$-naphthyl)butan-2-one

The hydrogenation described in Example 1 was repeated using the alternative catalyst 5% rhodium on alumina. It was found that the theoretical uptake of hydrogen required 28 hours and the yield obtained was 75%.

EXAMPLE 4

Preparation of 4-(6$^1$-methoxy-2$^1$-naphthyl)butan-2-one p-Methylbenzyl acetoacetate (18.0 g, 0.0874 mole), 6-methoxy-2-naphthaldehyde (14.8 g, 0.0796 mole), Cyclohexane (200 ml) and a catalytic quantity of piperidinium acetate (0.8 g) were refluxed together for 2.5 hours and the water collected in a Dean and Stark receiver. Ether (170 ml) was added, the mixture cooled to -5° giving the title compound (10.7 g) in 36% yield. Further crops were isolated by cooling and by concentration and crystallisation from ether to give finally a total of 22.6 g of the title compound in 75.9% yield as a yellow solid, melting point 78°–80°.

3-p-Methylbenzyloxycarbonyl-4-(6$^1$-methoxy-2$^1$-naphthyl)but-3-en2-one (5 g, 0.0134 mole), 10% palladium on charcoal (0.25 g) and ethylacetate (30 ml) were shaken together under a hydrogen atmosphere until hydrogen uptake had ceased. Removal of the catalyst by filtration and solvent by evaporation gave a white solid which was recrystallised from ethanol (15 ml) to yield in two crops a total of 2.6 g of 4-(6$^1$-methoxy-2$^1$-naphthyl)butan-2-one (85.3%) as a white solid, melting point 78.5°–80°. The overall yield from 6-methoxy-2-naphthaldehyde to 4-(6$^1$-methoxy-2$^1$-naphthyl)butan-2-one using p-methylbenzyl acetoacetate was 64.7%.

The p-methylbenzyl acetoacetate was prepared as follows:

Ethyl acetoacetate (22.5g, 0.173 mole) and p-Methylbenzyl alcohol (18.3 g., 0.15 mole) were heated together at about 200° and the liberated ethanol collected by distillation. The reaction mixture was then fractionally distilled, the final fraction boiling with a head temperature of 118°–122° at 1.0 mmHg being p-Methylbenzyl acetoacetate. (Yield 26 g.)

EXAMPLE 5

Preparation of 4-(6$^1$-Methoxy-2$^1$-naphthyl)butan-2-one p-Methoxybenzyl acetoacetate (25 g 0.1126 mole), 6-methoxy-2-naphthaldehyde (18.6 g 0.1 mole), cyclohexane (200 ml) and piperidinium acetate (1 g) were refluxed together for 1.5 hours and the water collected in a Dean and Stark receiver. Ether (200 ml) was added and the precipitated oil allowed to crystallise overnight to yield 31 g (79.5%) of the title compound as a yellow solid, melting point 93.5°–95.5°.

5 g of 3-p-Methoxybenzyloxycarbonyl-4-(6$^1$-methoxy-2$^1$-naphthyl)but-3-en-2-one was hydrogenated as in Example 4 to yield 2.3 g, (78.7%) of 4-(6$^1$-methoxy-2$^1$-naphthyl)butan-2-one as a white solid, melting point 78.5°–80°. The overall yield from 6-methoxy-2-naphthaldehyde to 4-(6$^1$-methoxy-2$^1$-naphthyl)butan-2-one using p-methoxybenzyl acetoacetate was 62.6%.

The p-methoxybenzyl acetoacetate was prepared as follows:

p-Methoxybenzyl alcohol (27.6 g 0.2 mole) and ethyl acetoacetate (32 g, 0.246 mole) were heated together to about 190° and the ethanol so formed collected by distillation. The reaction mixture was fractionally distilled and p-methoxybenzyl acetoacetate collected at a head temperature of 126°–132° and vacuum of 0.3 mm Hg. Yield 39 g (87.7%).

EXAMPLE 6

Preparation of 4-(6$^1$-Methoxy-2$^1$-naphthyl)butan-2-one

Benzhydryl acetoacetate (9 g, 0.0336 mole), 6-methoxy-2-naphthaldehyde (5 g, 0.0269 mole), cyclohexane (80 ml) and piperidinium acetate (0.26 g) were refluxed together for 1.5 hours and the water collected in a Dean and Stark receiver. Ether (60 ml) was added and the mixture cooled to 0° to yield 9.4 g (80%) of the title compound in two crops, melting point 124°–126°.

5 g, 0.0115 mole of benzhydryloxycarbonyl-4-(6$^1$-methoxy-2-naphthyl(but-3-en-2-one was hydrogenated as in Example 4 to yield 2.1 g (80.3%) of 4-(6$^1$-methoxy-2-naphthyl)butan-2-one as a white solid, melting point 79°–80.5°. Overall yield from 6-methoxy-2-naphthaldehyde to 4-(6$^1$-methoxy-2-naphthyl)butan-2-one using benzhydryl acetoacetate is 64.2%.

The benzhydryl acetoacetate was preparaed as follows:

Benzhydrol (20 g, 0.1087 mole) and ethyl acetoacetate (13 g, 0.1 mole) were heated together to 170° and the ethanol so formed removed by distillation. Fractional distillation at 1.0 mm Hg yielded 10.5 g, 39% of benzhydryl acetoacetate as a colourless liquid which later solidified, melting point 44°–54°.

We claim:

1. A process for the preparation of 4-(6$^1$-methoxy-2$^1$-naphthyl)butan-2-one which process comprises the hydrogenation of a compound of the formula (I):

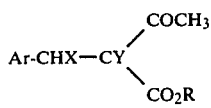

(I)

wherein Ar is a 6-methoxy-2-naphthyl group; X and Y represent a second bond between the carbon atoms to which they are attached; and —CO$_2$R is a carboxylic acid ester group convertible to a CO$_2$H group by catalytic hydrogenation in the presence of a supported, noble, metal catalyst at about atmospheric pressure.

2. A process as claimed in claim 1 wherein R is a benzyl or substituted benzyl group of the sub-formula (a), (b) or (c):

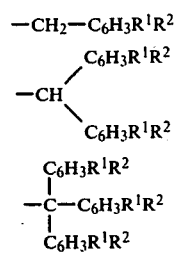

wherein R$^1$ and R$^2$ are independently hydrogen or halogen atoms or lower alkyl, lower alkoxyl, or nitro.

3. A process as claimed in claim 1 wherein R is a benzyl, p-methoxybenzyl, p-bromobenzyl, p-methylbenzyl or p-chlorobenzyl group.

4. A process as claimed in claim 1 further characterised in that the compound of the formula (I) is prepared by the reaction of 6-methoxy-2-naphthaldehyde with a compound of the formula (III):

$$CH_3.CO.CH_2.CO_2R \qquad (III)$$

wherein R is defined as in relation to formula (I).

5. A process as claimed in claim 1 wherein the hydrogenation is carried out using a pressure of hydrogen of 0.9 to 1.5 atmospheres in the presence of a noble metal catalyst.

6. A process as claimed in claim 5 wherein the catalyst is palladium.

7. A process as claimed in claim 5 wherein the hydrogenation is effected in solution in ethyl-acetate.

8. A process as claimed in claim 1, wherein the compounds of formula (I) are converted in a single step to the compound to be produced.

9. A process as claimed in claim 8, wherein the compounds of formula (I) are converted by hydrogenation at a pressure of about 0.5 to 4 atmospheres of hydrogen in the presence of a noble metal catalyst and in a solvent at a temperature of about 0° C. to 35° C.

* * * * *